United States Patent [19]
Walker et al.

[11] 4,382,002
[45] May 3, 1983

[54] DRILLING FLUIDS CONTAINING AN ADDITIVE COMPOSITION

[75] Inventors: Thad O. Walker, Humble, Tex.; Darrell W. Brownawell, Scotch Plains; Antonio Gutierrez, Mercerville, both of N.J.

[73] Assignee: Exxon Research & Engineering Co., Florham Park, N.J.

[21] Appl. No.: 277,053

[22] Filed: Jun. 24, 1981

[51] Int. Cl.$^3$ .............................................. C09K 7/02
[52] U.S. Cl. ................................ 252/8.5 C; 252/49.3
[58] Field of Search .............. 252/8.5 C, 8.5 A, 8.5 P, 252/8.55 R, 48.2, 48.6, 49.3

[56] References Cited
U.S. PATENT DOCUMENTS

| | | | |
|---|---|---|---|
| 3,027,324 | 3/1962 | Rosenberg | 252/8.5 |
| 3,761,410 | 9/1973 | Mondshine et al. | 252/8.5 |
| 4,053,422 | 10/1977 | Walker | 252/8.5 |
| 4,064,056 | 12/1977 | Walker et al. | 252/8.5 C |
| 4,141,840 | 2/1979 | Walker et al. | 252/8.5 |

Primary Examiner—Herbert B. Guynn
Attorney, Agent, or Firm—Roland A. Dexter

[57] ABSTRACT

Aqueous drilling fluids containing a minor amount of an additive composition featuring mono- and di-esters of $C_{12}$–$C_{50}$ aliphatic hydrocarbon substituted succinic acids or anhydrides, such as octadecenyl succinic anhydride with thio-bis-alkanols such as dithiodiethanol. Such fluids are especially useful where reduced torque drilling fluids are needed. Another embodiment of this invention relates to a method of drilling utilizing the above-described fluids.

5 Claims, No Drawings

DRILLING FLUIDS CONTAINING AN ADDITIVE COMPOSITION

This invention relates to aqueous drilling fluids. More particularly, this invention relates to aqueous drilling fluids having incorporated therein a minor amount of an ester of thio-bis alkanols and alkenyl succinic acid or anhydride which are especially effective as lubricity modifiers for drilling fluids. In another embodiment this invention is directed to an improved drilling operation employing the modified drilling fluids described above.

BACKGROUND OF THE INVENTION

In a drilling operation, such as in a rotary drilling operation, a drilling fluid is forced down the drill string, about the drill bit at the bottom of the borehole and then back up to the surface. The drilling fluid employed in such a drilling operation usually is an aqueous drilling fluid and is compounded of various materials in order to impart certain desirable physical and chemical properties to the drilling fluid. For example, there is usually incorporated in an aqueous drilling fluid a hydratable clayey material, such as a bentonite clay, to impart desirable viscosity and gel strength properties to the drilling fluid so as to better enable the drilling fluid to carry away the drilling cuttings from the bottom of the borehole. Other materials such as weighting agents, e.g., barium sulfate, are employed to increase the density of the drilling fluid so as to make the drilling operation more effective and safer by overcoming the fluid pressure within the formation being drilled. Other materials such as water loss improving agents, e.g., carboxymethylcellulose, hydrolyzed starch, etc. are added to reduce the loss of fluid from the drilling fluid into the formation during the drilling operation. Still other materials such as corrosion inhibitors, bactericides and drill bit lubricants are incorporated in the drilling fluid in order to improve the drilling operation and the drilling fluid.

Although a wide variety of aqueous drilling fluids containing materials designed to increase the lubricity of these fluids have been proposed and used in the field such as: vegetable oils including soybean and rice oil; tall oil; sodium salts of petroleum sulfonic acids and resin acids (see U.S. Pat. No. 4,064,056); and polyethoxylated tetralkylacetylenic diols, it remains essential that lubricity of said drilling fluids be further improved to reduce the energy requirement of said drilling and abrasion of the drilling equipments.

It is therefore an object to provide an additive composition for drilling fluids that reduces its drilling torque.

SUMMARY OF THE INVENTION

It has been discovered that the addition of a minor amount of mono- or di-esters, and mixtures thereof, formed by the reaction of (a) thio-bis-alkanols of the formula:

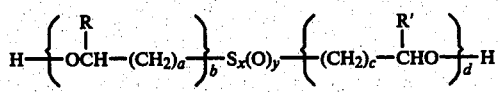

wherein R and R' each independently may be hydrogen, methyl or ethyl, x may be 1–4, y may be 0, 1 or 2, a, b, c, and d each independently may be 1–3; with (b) 1 or 2 moles, per mole of the thio-bis-alkanol, of an aliphatic hydrocarbon substituted succinic acid or anhydride or mixtures thereof wherein the aliphatic hydrocarbon group contains a total of from about 12 to 50, preferably 14 to 30, optimally 18 to 22, carbon atoms to an aqueous drilling fluid substantially increases the lubricity of said drilling fluid as measured, for example, by torque reduction.

Preferred are aqueous drilling fluids containing from 0.1 to 10, usefully 0.5 to 5, optimally 1 to 3, pounds per barrel of drilling fluid of a hemi- or di-ester of said thio-bis-alkanol reacted with from 1 to 2 moles of a $C_{14}$ to $C_{30}$, preferably $C_{18}$ to $C_{22}$ alkenyl succinic acid or anhydride.

DETAILED DESCRIPTION OF THE INVENTION

As used herein, the term "monoester" or "hemiester" refers to products made from equimolar proportions of said thio-bis-alkanol and a succinic acid or anhydride, that is, one free hydroxyl group remains, while the term "diester" as used herein refers to those products wherein each hydroxyl group of the thio-bis-alkanol is esterified with a hydrocarbyl substituted or polyolefin substituted succinic acid or anhydride. In either case, a succinic acid moiety remains, i.e., a —C(O)OH group, but this may be neutralized with metals or amines as described herein below to form useful salt derivatives.

The hydrocarbyl succinic acids or anhydrides are per se known in the art and the commonly used anhydride may be represented by the formula:

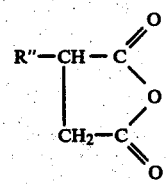

wherein R" is $C_{12}$-$C_{50}$ aliphatic group, such as in alkyl, alkenyl, isoalkyl, isoalkenyl or cycloalkyl hydrocarbyl group. Oligomers containing 12 to 50 carbon atoms are also suitable as the aliphatic hydrocarbyl group such as oligomers of $C_2$-$C_5$ monoolefins such as isobutene.

The aliphatic hydrocarbyl group may be an unsubstituted hydrocarbon group or it may contain substituents such as chlorine, bromine, sulfur, phosphorous or oxygen which will not affect the utility of the final mono- or di-ester product. A preferred substituent is sulfur as exemplified by 2-octadecylthio succinic anhydride.

These compounds may be prepared by the reaction of maleic anhydride with olefins, oligomeric polyolefins, or with chlorinated derivatives thereof using techniques known in the art. Succinic acids are readily produced by hydrolysis of the corresponding anhydride. Especially preferred in preparing the novel mono- and di-ester compounds of the present invention are $C_{18}$-$C_{22}$ alkenyl succinic anhydrides, such as octadecenyl succinic anhydride.

The term thio-bis-alkanol as used herein is understood to represent those ester-forming diol compounds of the formula:

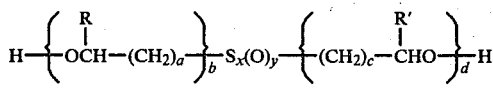

wherein R and R' each independently may be hydrogen methyl or ethyl; x may be 1–4; y can be 0, 1 or 2; and a, b, c, and d each independently may be 1–3. Thus, if y is 0, the bridging unit is —S— or $S_2$, $S_3$ or $S_4$. When y is 1 or 2, the bridging unit is a sulfinyl or sulfonyl functional group. If b and d are greater than 1, then the formula is meant to express ethoxylated derivatives of such alcohols.

Preferred embodiments are those thio-bis-alkanols within the foregoing formula wherein a, b, and c and d are each 1 or 2 and y is 0 with R being H or $CH_3$. Specific compounds include 2,2'-dithiodiethanol 2,2'-thiodiethanol, di(2-hydroxypropyl)disulfide, 3,3'thiodipropanol and 2,2'-sulfonyldiethanol.

Formation of the mono- and di-esters of the present invention proceeds by reacting the appropriate quantities of anhydride (or acid) and thio-bis-alkanol with or without an inert organic solvent diluent and heating and stirring the mixture at about 50° to 150° C. until esterification of the anhydride is complete. Equimolar quantities of each reactant will provide mainly the mono- (or hemi-) ester and reaction of 2 moles of hydrocarbon substituted succinic acid or anhydride per mole of thio-bis-alkanol will provide the di-ester material. Also, products useful in the present invention encompass mixtures of such mono- and di-esters.

Insofar as yields are concerned, the reaction of an equimolar ratio of thio-bis-alkanol and hydrocarbon succinic anhydride will provide a product containing about 80% mono-ester and about 20% di-ester. The di-ester is produced in somewhat higher yields, about 90% of the product being di-ester and about 10% mono-ester when the mole ratio of succinic anhydride to thio-bis-alkanol is 2:1. The novel di-ester compounds of this invention are particularly preferred embodiments exhibiting generally better thermal and oxidative stability and offering better friction-reducing properties.

In the case of a di-ester compound, it is suitable to use succinic anhydrides having less than $C_{12}$ hydrocarbon substituent so long as the total number of carbon atoms of the hydrocarbon substituents on the succinic moiety of the ester compounds is at least 12, e.g. symmetrical di-esters based upon two moles of decenyl succinic anhydride or an asymmetrical di-ester based upon a mole of a $C_3$ hydrocarbon substituted succinic anhydride and a mole of a $C_{16}$ hydrocarbon substituted succinic anhydride.

Further embodiments of the present invention are metal and amine salts of either the mono- or di-ester, formed by reaction with the free succinic acid moiety which is present in either the mono- or di-ester of this invention.

The metal salts of the mono- and di-esters of this invention are preferably the zinc, calcium, magnesium, molybdenum and ammonium salts formed by simply reacting a free succinic acid group of the mono- or di-ester with a suitable metal such as zinc, copper or molybdenum acetate or an amine in the presence of xylene and azeotroping acetic acid.

Amine salts may be generally based upon an amino or polyamino compound which is reactive toward the free carboxylic moiety. Suitable amines include primary or tertiary secondary hydrocarbyl and aliphatic hydrocarbyl mono- or polyamines having about 1 to 30 carbon atoms, such as methyl and ethyl amine, aniline, diethanolamine, dipropylamine, ethylene diamine, morpholine, phenylene and naphthalene diamines and the like.

The amount of the hemi- or di-ester or salts thereof added to the well drilling fluid may be only a minor but sufficient amount to substantially increase the lubricity of the said drilling fluid as measured, for example, by torque reduction. The amount to be added to the well drilling fluid is in the range of from 0.1 to 10, preferably 0.5 to about 5, pounds per barrel of drilling fluid, optimally from about 1 to about 3 pounds per barrel.

It has been found that the drilling fluids of the present invention exhibit a high degree of lubricity and little or no abnormal distortion of mud properties.

The additives are generally introduced into the drilling mud as a hydrocarbon solution containing broadly from at least 2 to 99, preferably 30 to 70, optimally 40 to 50, weight % additive based on the total weight of the solution. The additive can also be introduced neat, i.e., only additive, in the drilling mud when significantly dispersible into the aqueous mud. If desired, other additives such as water loss improving agents, corrosion inhibitors, bactericides, etc. can be introduced as part of the additive-solvent package into the drilling mud.

Suitable hydrocarbon solvents include: mineral oils, particularly those paraffin base oils of good oxidation stability with a boiling range of from 200° C. to 400° C. such as Mentor 28 ® sold by Exxon Chemical Americas, Houston, Texas; diesel and gas oils; and heavy aromatic naphtha. Preferred are those above-referenced paraffin base oils.

The invention is further illustrated by the following Examples which are not to be considered as limitative of its scope.

EXAMPLE 1

This Example shows the preparation of 6-hydroxy-3,4-dithiohexyl 2-octadecenyl succinic acid ester.

0.2 mole (70 g.) of 2-octadecenyl succinic anhydride and 0.2 mole (30.8 g.) of 2,2-dithiodiethanol were combined and heated gradually to 140° C. The mixture was stirred at this temperature until IR analysis showed the absence of an anhydride carbonyl absorption. Elemental analysis showed 12.2% S; theory for a mono-ester is 12.7% S.

EXAMPLE 2

This example shows the preparation of a di-ester of 2-octadecenyl succinic anhydride with 2,2'-thio-bis-ethanol.

About 636 g (1,81 mole) of 2-octadecenyl succinic anhydride were heated to 150° C. and 111 g (0.91 mole) of 2,2'-thio-bis-ethanol were added dropwise for a period of one half hour. The mixture was stirred at this temperature for another half hour or until the IR analysis showed the absence of carbonyl anhydride band.

EXAMPLE 3

This example shows the preparation of the di-ester of 2-octadecyl-thio succinic anhydride with 2-2'-dithio-diethanol.

About 57 g (0.15 mole) of 2-octadecylthio succinic anhydride (prepared with the addition of 1-octadecyl mercaptan to maleic anhydride, or via the addition of mercapto succinic acid to 1-octadecene) were dissolved in 50 ml of tetrahydrofuran and combined with 11.6 g (0.075 mole) of 2,2'-dithiodiethanol. The THF solution was gradually heated and the THF was distilled off. The residue was heated to 140° C. and kept at this temperature for one half hour. The infrared analysis showed the absence of a carbonyl anhydride absorption band.

For a complete description of the preparation of the additives which provide enhanced lubricity to drilling muds reference should be made to U.S. patent application PT-483, Ser. No. 194,067, filed Oct. 6, 1980 now abandoned, of common assignee which is incorporated herein fully by reference thereto.

EXAMPLE 4

The lubricity activity of the formulations of the invention are shown in Table I following by comparison with a base mud. The base mud is prepared from 20 to 25 pounds of bentonite [5 to 7 wt. %], 4 to 6 pounds of lignosulfonate [1 to 2 wt. %] and sufficient sodium hydroxide to adjust the pH to 9.5 to 10.5 per barrel of water. This is the basic drilling mud to which the lubricity additives taught here are added to produce the drilling muds of much enhanced lubricity as seen from the following Table I.

The rheology data of Table I was determined on a Fann model 35 Viscousimeter purchased from Fann Industries of Houston, Texas. The torque data was determined on a Baroid Lubricity Tester available from the Baroid Division of N. L. Industries, Houston, Texas.

TABLE I

| | Additive Conc.[1] Lb/BBl | rpm 600 | rpm 300 | Plastic Viscosity | Yield Point | Gel[2] | pH | % Torque[3] Reduction |
|---|---|---|---|---|---|---|---|---|
| Base | | 49 | 27 | 22 | 5 | 1-2 | 10 | — |
| Base + Product Ex. 1 | 2 | 57 | 32 | 25 | 7 | 2-2 | 10 | 71.1 |
| Base + Product Ex. 3 | 2 | 53 | 30 | 23 | 7 | 1-1 | 10 | 78.9 |
| Base + Product Ex. 2 | 2 | 60 | 34 | 26 | 8 | 2-2 | 10 | 91.7 |
| Base + Commercial Product[1] | 2 | — | — | — | — | — | — | 70 |
| Base + Commercial Product[2] | 2 | — | — | — | — | — | — | 75 |

[1]All additives added as a 50% concentrate in a paraffinic hydrocarbon
[2]Deflection on Viscousimeter at 3 rpm initially and after 10 minutes
[3]As measured by Baroid Lubricity Tester The data shows that the Products of Example 1, Example 2, and Example 3 reduced the torque significantly with the Product of Example 2 providing the most reduction in torque. The rheology of the muds changes slightly but the changes do not present any viscosity problems.

The invention in its broader aspect is not limited to the specific details shown and described and departures may be made from such details without departing from the principles of the invention and without sacrificing its chief advantages.

We claim:

1. An alkaline drilling mud comprising particles of clayey material suspended in sufficient water to render it circulatable and an effective amount of an ester compound formed by the reaction of:
   (a) a thio-bis-alkanol of the formula:

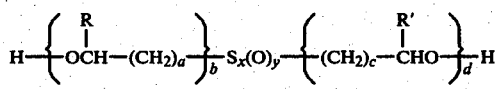

wherein R and R' each independently may be hydrogen, methyl or ethyl, x may be 1-4, y may be 0, 1 or 2, a, b, c, and d, each independently maybe 1-3; with (b) 1 to 2 moles, per mole of the thio-bis-alkanol, of an aliphatic hydrocarbon substituted succinic acid or anhydride wherein the aliphatic hydrocarbon group contains from about 12 to 50 carbon atoms whereby the drilling torque of said mud is reduced.

2. A mud according to claim 1 wherein said ester compound is the mono-ester of dithiodiethanol with octadecenyl succinic anhydride.

3. A mud according to claim 1 wherein said ester compound the di-ester of dithiodiethanol with octadecenyl succinic anhydride.

4. In a process for drilling a well with well drilling tools wherein there is circulated in the well an alkaline drilling mud containing particles of clayey material suspended in sufficient water to render the same circulatable, the method of reducing the drilling torque of the drilling mud comprising adding to each barrel of said mud from 0.1 to 10 pounds of an ester compound formed by the reaction of:
   (a) a thio-bis-alkanol of the formula:

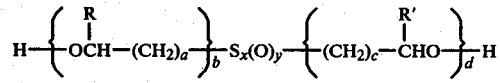

wherein R and R' each independently may be hydrogen, methyl or ethyl, x may be 1-4, y may be 0, 1 or 2, a, b, c, and d, each independently maybe 1-3; with (b) 1 to 2 moles, per mole of the thio-bis-alkanol, of an aliphatic hydrocarbon substituted succinic acid or anhydride wherein the aliphatic hydrocarbonyl group contains from about 12 to 50 carbon atoms whereby the drilling torque of said mud is reduced.

5. An additive combination for increasing the lubricity of drilling muds consisting essentially of from 30 to 70 parts by weight of an ester compound dissolved in a hydrocarbon solvent, said ester compound being formed by the reaction of:
   (a) a thio-bis-alkanol of the formula:

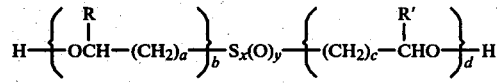

wherein R and R' each independently may be hydrogen, methyl or ethyl, x may be 1-4, y may be 0, 1 or 2, a, b, c, and d, each independently maybe 1-3; with (b) 1 to 2 moles, per mole of the thio-bis-alkanol, of an aliphatic hydrocarbon substituted succinic acid or anhydride wherein the aliphatic hydrocarbon group contains from about 12 to 50 carbon atoms whereby the drilling torque of said mud is reduced.

* * * * *